US00PP08956P

United States Patent [19]

Peters

[11] Patent Number: Plant 8,956

[45] Date of Patent: Oct. 25, 1994

[54] PEACH TREE "AUGUST LADY"

[76] Inventor: Ron D. Peters, 41018 Road 56, Reedley, Calif. 93654

[21] Appl. No.: 103,191

[22] Filed: Aug. 6, 1993

[51] Int. Cl.[5] ..... A01H 5/00
[52] U.S. Cl. ..... Plt./43.2
[58] Field of Search ..... Plt. 43.2

*Primary Examiner*—Patricia R. Moody
*Attorney, Agent, or Firm*—Godfrey & Kahn

[57] ABSTRACT

A new and distinct variety of peach tree denominated varietally as "August Lady" and which is somewhat similar to the Summer Lady peach tree [U.S. Plant Pat. No. 5,865] with which it is most closely related, but which is distinguished therefrom and characterized as to novelty by producing fruit which are mature for commercial harvesting and shipment approximately August 2 through August 9 in central California, these dates being approximately 12 days later than that of Summer Lady peach tree at the same geographic location.

1 Drawing Sheet

BACKGROUND OF THE NEW VARIETY

The present invention relates to a new and distinct variety of peach tree which is denominated varietally as "August Lady" and more particularly, to such a peach tree which bears a freestone, late maturing, high quality fruit which has a firm, crisp flesh texture at commercial maturity, and which further is principally characterized as to novelty by a date of ripening of approximately August 2 through August 8 at Dinuba, Calif.

Fruit growers have recognized for some period of time that the relative dates that various varieties of peaches become ripe for harvesting is of extreme importance. In particular, it has long been known that it is desirable to provide a peach tree that bears fruit during a portion of the season later than other varieties of peach trees with which it most closely resembles, whereby the fruit produced by such trees can be sent to market at a time when competition is at a minimum and the best price can be negotiated. Further, large scale agricultural businesses have long understood that additional economic benefits can be attained if the harvesting period of a period orchard is spread out over a longer period of time inasmuch as the capital expenditures required to harvest and transport produce from the orchard can be extended over the same period of time thereby resulting in an overall lower cost of the final product and simultaneously increasing the uniformity of production throughout the entire season.

The new and distinct variety of peach tree disclosed herein is characterized as to novelty by producing fruit which are somewhat similar in their physical characteristic to the "Summer Lady" peach tree [U.S. Plant Pat. No. 5,865], of which the new variety is a chance mutation, but which is distinguished therefrom by producing fruit which are mature for harvesting in shipment approximately two weeks later than the "Summer Lady" peach tree at the same geographic location in the San Joaquin Valley of Central California.

ORIGIN AND ASEXUAL REPRODUCTION OF THE NEW VARIETY

The inventor has spent a substantial portion of his professional life engaged in farming operations. In this regard, the applicant, during routine orchard operations in the summer of 1988, discovered what appeared to be a whole tree mutation of a Summer Lady peach tree [U.S. Plant Pat. No. 5,865] growing within the cultivated area of his commercial orchard which is located at 5389 Avenue 408, in Reedley, Calif. The fruit produced by the mutation was noted at that time to have desirable characteristics. More particularly, it was noted that the mutated tree produced fruit which were mature for harvesting and shipment approximately two weeks later than the remainder of the trees in the same block of "Summer Lady" peach trees. The inventor marked the mutated tree for subsequent observation. To determine whether the traits of the newly discovered variety werew true, the inventor in January, 1991 removed bud wood from the mutated trees and had it grafted it to test trees which were then planted in an orchard located at 41166 Road 56, Reedley, Calif. The inventor has observed these test trees and the original mutated tree, and has evaluated the fruit produced therefrom and it has been subsequently determined that the fruit produced from these test trees have the same identical characteristics as that produced by the original mutated tree.

SUMMARY OF THE NEW VARIETY

The "August Lady" peach tree hereof is characterized principally as to novelty by bearing fruit which have an appearance, and favor which is similar to the fruit produced by the "Summer Lady" peach tree [U.S. Plant Pat. No. 5,865] from which it was derived as a chance mutation, and wherein the fruit produced by the Summer Lady peach tree is mature for harvesting and shipment under the ecological conditions existing in central California from approximately July 14 through July 20, and wherein the new variety "August Lady" is distinguishable therefrom by producing fruit which are ripe for commercial harvesting and shipment under the same ecological conditions during the period August 2 through August 8.

BRIEF DESCRIPTION OF THE DRAWINGS

The accompanying drawing is a color photograph of a characteristic twig bearing typical leaves which displays both the dorsal and ventral coloration thereof. Further, the photographs display several peaches showing their external coloration sufficiently matured for harvesting and shipment; and a peach divided in the axial plane to show the flesh and pit characteristics all of the subject variety.

DETAILED DESCRIPTION

Referring more specifically to the pomological details of this new and distinct variety of peach tree, the following has been observed under the ecological conditions prevailing in the orchard of origin of the inventor which is located in Dinuba, Calif. All major color code designations are by reference to the dictionary of color by Maerz & Paul, First Edition and which was published in 1930. Common color names are also used occasionally.

TREE

Size:
*Generally.*—Average.

Form: Upright, to upright-spreading growth. The tree is trained to a standard open-vase system. Eventual density is determined by pruning practices.
*Regularity of bearing.*—Regular, and hardy under normal San Joaquin Valley climatic conditions.

Productivity: Productive.

Vigor:
*Generally.*—Vigorous.

Shoot extension:
*Generally.*—Shoot extensions have been observed in the top of the trees and range in length from approximately 3–4.5 feet (0.914 –1.219 meters), annually.

Trunk:
*Thickness.*—Average.
*Surface texture.*—Average as compared to the species.
*Lenticels — Generally.*—As a general matter, the lenticels are numerous, flat and have an oval shape.
*Lenticels — Size.*—Approximately 6 to 8 millimeters in length.

Bark:
*Color.*—Gray — brown [15-A-7 Soapstone].

Branches:
*Size.*—Average.
*Surface texture.*—Relatively smooth.
*Color.*—The color of mature two-year old shoots is a medium brown [7-H-12 Mohawk Brown].
*Color — current season shoots.*—Normally a pale green [21-L-5 Grass Green].
*Shoot tips — color.*—Bright shiny green [19-L-4].

LEAVES

Size:
*Generally.*—Large.
*Average length.*—Approximately 19.4 through 21.9 centimeters, including the petiole.
*Average width.*—Approximately 4.8 through 5.5 centimeters.
*Thickness.*—Average.

Leaf form:
*Generally.*—Lanceolate.
*Leaf apex.*—Form — Acuminate. The apex often appears slightly twisted, sideways.

Color:
*Upper leaf surface.*—Dark green [24-H-6].
*Lower leaf surface.*—Gray — green [23-J-7].

Leaf margins:
*Marginal form.*—Crenate with large, low and somewhat irregular shaped crenations appearing. At mid-margin, numerous double crenations can also be seen. The leaf margins are considered moderately undulate.

Leaf petiole:
*Generally.*—Medium in size.
*Length.*—Approximately 11 to 15 millimeters
*Thickness.*—Approximately 2 to 2.5 millimeters.
*Color.*—Light green [20-J-5 Absinthe Green]. This color is darker within the petiole groove [21-J-7].

Leaf glands:
*Size.*—Medium.
*Form.*—Mixed.
*Numbers.*—From 0 to 4 glands can be seen on the petiole.
*Position.*—Alternate.
*Shape.*—Reniform and globose glands may both be present. In this regard, globose glands usually are stalked.
*Lower leaf margin.*—Generally — An additional 1 to 3 glands may be present along the lower leaf margin. The glands located along the margin are usually reniform in shape.
*Color.*—Young glands — Shiny, and yellow-green, [19-L-2, Javel Green]. The glands become darker with senescence.

Leaf stipules:
*Size.*—Generally considered large.
*Length.*—Approximately 12 to 14 millimeters.
*Shape.*—Considered linearly lanceolate in form.
*Margins.*—Shape — Serrate.
*Color.*—New Stipules — Glossy green, [18-L-7]. This color becomes darker with advancing senescence. The stipules are considered early deciduous.

FLOWERS

Date of bloom:
*Generally.*—The date of bloom is considered average and perhaps slightly later than the date of full bloom of other common commercial peach cultivars growing in the same geographical location. Date of full bloom at Dinuba, Calif. was Mar. 7, 1993. The date of full bloom of the subject variety is substantially identical to the "Summer Lady" peach tree of which the new variety is a whole tree mutation.

Flower buds:
*Generally.*—The flower buds are considered hardy under normal San Joaquin Valley climatic conditions.
*Size.*—Generally, considered large.
*Form.*—Conic.
*Position.*—The buds are considered relatively free from the stem.
*Bud scales.*—Surface texture — Pubescent.
*Bud color.*—Gray — brown, [15-C-8 Chukker Brown].

Generally:
*Size.*—Large.
*Type.*—Considered a showy flower.
*Diameter.*—Fully expanded — approximately 38 to 43 millimeters.
*Bloom quantity.*—Bloom density is considered average to slightly below average, as compared with other common peach cultivars.
*Number of flowers.*—1 to 2 flowers are present per node. Normally, however, two flowers appear.

Petals:

*Size.*—Generally — Large.
*Length.*—Approximately 18 to 21 millimeters.
*Width.*—Approximately 15 to 20 millimeters.
*Form.*—Generally — Broadly ovate.
*Numbers.*—Five.
*Color.*—The petals, when young, are generally a light pink, [1-E-1], and the basal portion of same is a darker rose — pink color, [1-H-4]. The petals become darker with advancing senescence, especially basally thereof.
*Claw — form.*—The claw is generally considered truncate.
*Claw — size.*—Medium to large.
*Claw — length.*—Approximately 2 to 3 millimeters.
*Claw — width.*—Approximately 1 to 1.5 millimeters.
*Margins.*—Form — Generally undulate.
*Petal apices.*—Shape — Usually elevated or domed.

Pedicel:
*Generally.*—Short.
*Length.*—Approximately 2.5 to 3 millimeters.
*Thickness.*—Approximately 1.5 millimeters.
*Color.*—Bright green, [18-L-4], and at times it may be overlain with maroon speckling or striping.
*Surface texture.*—Glabrous.

Nectaries:
*Color.*—Bright orange [9-I-12] and becoming slightly darker and dull in appearance with advancing senescence.

Calyx:
*Surface texture.*—Glabrous.
*Color.*—Generally maroon, [7-H-4], with some occasional green coloration appearing at the base thereof.

Sepals:
*Generally.*—The surface of the sepals is covered with moderately, long, grayish colored pubescence.
*Size.*—Large.
*Form.*—ovate.
*Color.*—Maroon, [7-C-4], with some green areas, [13-J-1], appearing especially along the sepal margins.

Anthers:
*Size.*—Medium.
*Color.*—Red, dorsally, [3-L-10, Goya Red], and tan or chamois colored, ventrally, [10-G-3, Cornsilk Yellow].
*Pollen production.*—Abundant.
*Pollen color.*—Yellow — gold, [10-L-4, Light Chrome Yellow].

Stamen:
*Length.*—Variable, approximately 16 to 22 millimeters. As general matter, most of the stamens are longer than the pistil.
*Filament color.*—Pale pink, [1-C-7, Pink No. 2]. This color becomes a dark rose-pink with advancing senescence [3-H-4 Persian Pink].

Pistil:
*Length.*—Variable, from 17–18 millimeters, including the ovary.
*Color.*—Pale, green-yellow, 17-H-2].
*Surface texture.*—Pubescent.

FRUIT

Maturity when described:
Ripe for commercial harvesting and shipment in 1992, approximately August 2 through August 8 at Reedely, Calif.

Size:
*Generally.*—Large and substantially uniform.
*Average cheek diameter.*—Approximately 79 to 82 millimeters.
*Average diameter in the suture plane.*—Approximately 82 to 88 millimeters.
*Average diameter in the axial plane.*—Approximately 69 to 75 millimeters.

Form:
*Generally.*—Uniform and asymmetrical, with one side of the fruit usually appearing larger than the other. The fruit is further oblate in its lateral aspect, and oval in its apical aspect.

Suture:
*Generally.*—The suture appears as a groove of moderate depth extending in a substantially continuous line from the base to the apex. As a general matter, the suture appears much more shallow over the basal shoulder. Further, a small amount of stitching may be present over the apical shoulder and along the area of the suture.
*Color.*—The suture appears to have no specific color unique to itself, but normally takes on the coloration of the underlying blush or ground color. In the event the underlying blush coloration is very dark red, the suture usually retains a lighter red-orange color in contrast to the surrounding garnet-red blush.

Ventral surface:
*Generally.*—Somewhat irregular and protruding. Further, the ventral surface is lipped. This is usually more noticeable on one side of the suture line.

Stem cavity:
*Size.*—Medium and rather broad.
*Width.*—Approximately 31 to 35 millimeters.
*Length.*—Approximately 33 to 39 millimeters.
*Depth.*—Approximately 12 to 16 millimeters.
*Shape.*—Broadly oval.
*Form.*—As a general matter, the ventral suture is often folded or clefted within the stem cavity. Additionally, slight indentations are often present in the basal shoulders where the fruit was pressed next to the bearing limb.

Fruit base:
*Form.*—Truncate.
*Base angle.*—Variable, appearing oblique to the fruit axis to nearly normal thereto.

Apex:
*Shape.*—Appearing generally rounded and having a depressed tip. The pistil point is usually apical and located along the suture line. The pistil is generally recessed below the height of the apical shoulders. A distinct depression is also present on both the dorsal and ventral sides of the apex, and along the suture line.

Stem:
*Length.*—Approximately 9–11 millimeters. Thickness — Approximately 3.5 to 4 millimeters.
*Color.*—Light green [20-L-3 Certosa Green].

Skin:
*Thickness.*—Average.
*Pubescence.*—Present. Normally it is fine, short and gray colored.
*Acidity.*—General neutral.
*Tenacious to flesh.*—Yes, at commercial maturity.
*Tendency to crack.*—Not observed.

Skin color:

*Generally.*—Uneven. Approximately 90% to 100% of the skin color includes a red blush. The blush pattern is variable from washed patterns to light amounts of striping. The lightest blush coloration is a light orange-red [3-C-11, Burmese Gold]. The darkest color is a red-orange [4-J-11, Canna Red]. Stripes and occasional washed areas have a very dark burgundy red, [7-L-5, Algerian Red] color. The ground color is a yellow-gold, [9-L-4, Sunflower Yellow]. The ground color is normally present only on the basal portion of the fruit and often only appears where the bearing limb was pressed next to fruit shoulder.

Flesh color:

*Generally.*—Amber-yellow, [9-K-5, Apricot Yellow].

*Fibers.*—Generally — Numerous light colored, and medium length fibers are present throughout the flesh.

*Stone cavity.*—Color — Garnet red, [7-J-6, Garnet Red]. This same color radiates into the flesh for a distance of approximately 7 to 15 millimeters. Occasional areas of red flecking are present in the flesh and are normally situated underneath the ventral suture area.

Flesh texture:

*Generally.*—The fruit is generally considered firm and fine textured and becomes juicy with advancing senescence.

Ripening:

*Generally.*—The fruit of the subject variety ripens and then softens initially over the basal shoulders.

Flavor:

*Generally.*—The fruit is considered to have rich flavor with moderate acidity. The flavor is considered a well-balanced blend of both sweetness and acidity.

Aroma: Moderate and pleasant.

Eating quality:

*Generally.*—Considered very good.

Use: A fresh market peach for both local and long distance markets.

STONE

Attachment: The subject variety is considered to be a full freestone peach.

Size:

*Length.*—Approximately 31 to 35 millimeters.

*Width.*—Approximately 27 to 30 millimeters.

*Thickness.*—Approximately 19 to 21 millimeters.

Fibers:

*Generally.*—Very little fiber attachment is evident especially at full maturity. Only a few short fibers are attached to the base of the stone and along the ventral suture.

*Form.*—Generally — Variable. From oval, to slightly obovate.

Base:

*Form.*—Truncate.

*Base angle.*—Variable, from very slightly oblique to the stone axis, to being positioned at approximately a normal attitude relative thereto.

Hilum:

*Size.*—Moderately large and distinct.

*Shape.*—Oval and wide, and having a relatively thick, grooved collar.

Apex:

*Form.*—Generally acute. The tip is variable and may appear acute, or occasionally acuminate.

Stone sides:

*Generally.*—The stone sides appear unequal.

Stone surface:

*Generally.*—Considered coarse. Laterally, the stone is unevenly pitted; and large, coalesced pits appear. The stone is coarsely grooved over the apical shoulders and near the ventral suture. Finer grooves also appear. These grooves converge basally.

Ventral edge:

*Generally.*—The ventral edge is quite broad and has a width dimension of approximately 5 to 6 millimeters at mid-suture. Several low wings are normally present along the ventral edge. The most prominent wing extends from mid-suture to the base. The maximum wing extension is approximately 4 to 6 millimeters from the stone body.

Dorsal edge:

*Generally.*—The dorsal edge most often appears as a deep, relatively wide groove which extends from the base to the apex and is subtended by two prominent, irregularly shaped ridges. The groove is normally most evident from mid-stone to the base and is generally more shallow near the apex. The Apical shoulder of the dorsal edge is usually substantially eroded and often concave in shape.

Stone color: Dry — Dark brown, [8-J-11, Montella Brown]. Slight purple staining is present on the stone surface, especially basally.

Tendency to split: Not observed.

Keep quality: Good.

*Resistance to disease.*—No particular susceptibilities were noted.

Although the new variety of peach tree possesses the described characteristics as a result of the growing conditions prevailing in the San Joaquin Valley of Central California, it is to be understood that variations of the usual magnitude and characteristics incident to growing conditions, fertilization, pruning and pest control would be expected.

Having thus described and illustrated my variety of peach tree, what I claim is:

1. A new and distinct variety of peach tree to be denominated varietally as "August Lady" substantially as illustrated and described, and which is characterized principally as to the novelty by its production of fruit which are somewhat similar in their overall characteristics to the fruit produced by the "Summer Lady" peach tree [U.S. Plant Pat. No. 5,865] from which the present variety was derived as a mutation, but which is distinguished therefrom and characterized principally as to novelty by producing fruit which are ripe for commercial harvesting and shipment approximately 12 days later than the fruit produced by the "Summer Lady" peach variety at the same geographical location in the San Joaquin Valley of Central California.

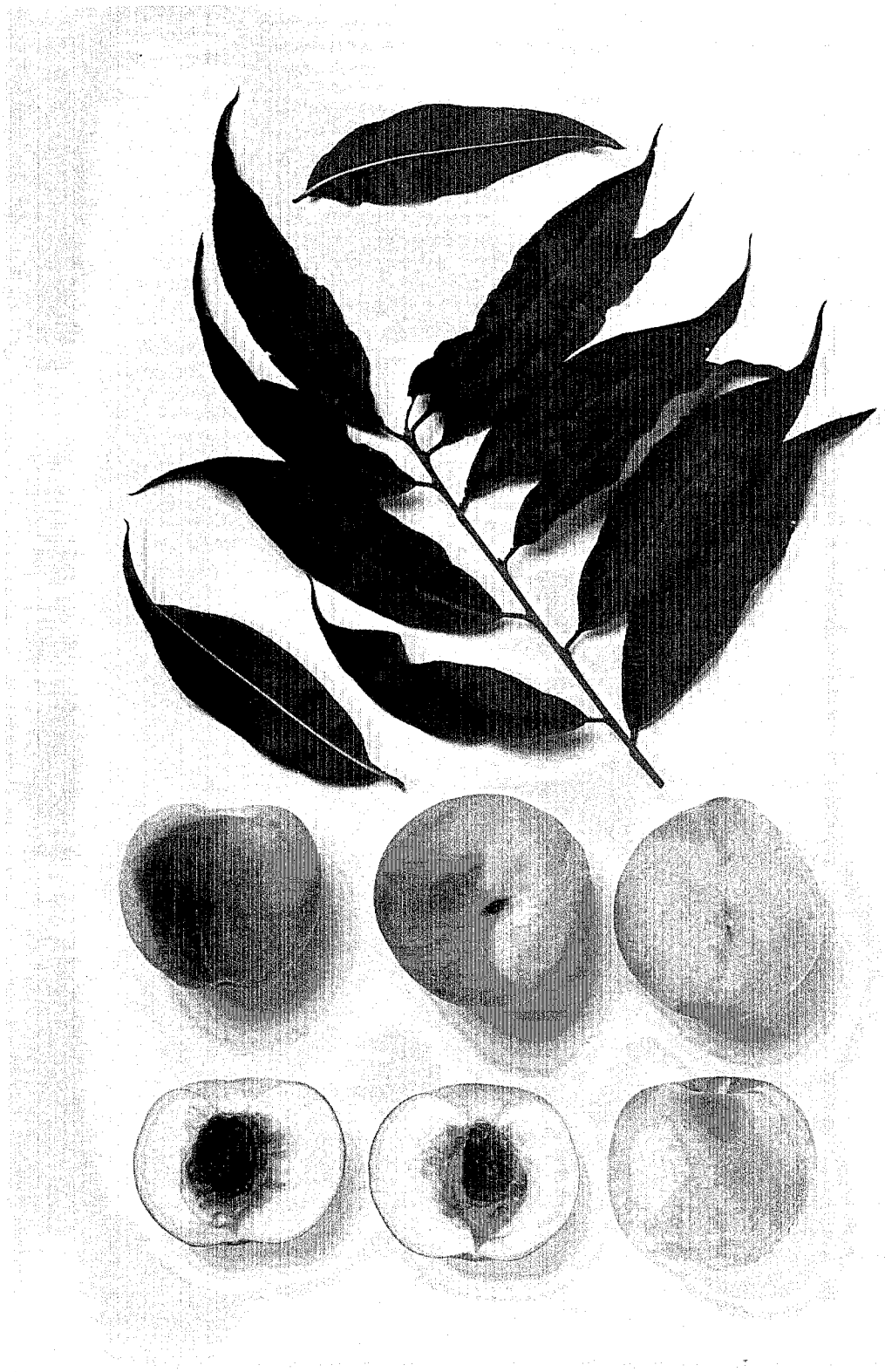

* * * * *